United States Patent [19]

Baumann et al.

[11] 4,322,413
[45] Mar. 30, 1982

[54] 1,2,3,5-THIATRIAZOLIDIN-4(2H)-ONE-1,1-DIOXIDE PHOSPHORIC ACID DERIVATIVES AND THEIR USE FOR COMBATING PESTS

[75] Inventors: Annegrit Baumann, Mannheim; Karl Kiehs, Lampertheim; Gerhard Hamprecht, Weinheim; Arno Lange, Mannheim; Heinrich Adolphi, Limburgerhof, all of Fed. Rep. of Germany

[73] Assignee: BASF Aktiengesellschaft, Fed. Rep. of Germany

[21] Appl. No.: 222,891

[22] Filed: Jan. 6, 1981

[30] Foreign Application Priority Data

Feb. 4, 1980 [DE] Fed. Rep. of Germany ....... 3003977

[51] Int. Cl.³ .................... A01N 57/16; C07F 9/65
[52] U.S. Cl. .................................... 424/200; 548/112; 548/125
[58] Field of Search ................. 548/112; 424/200

[56] References Cited

U.S. PATENT DOCUMENTS 2,984,669  5/1961  Brähler et al. .

FOREIGN PATENT DOCUMENTS 819998  11/1951  Fed. Rep. of Germany .
2349755  4/1974  Fed. Rep. of Germany .

OTHER PUBLICATIONS

Bartholomew et al., Chem. Abst., 1978, vol. 88, No. 22842 v and 22848 b.

*Primary Examiner*—Henry R. Jiles
*Assistant Examiner*—Natalia Harkaway
*Attorney, Agent, or Firm*—Keil & Witherspoon

[57] ABSTRACT

Heterocyclic phosphoric acid derivatives of the formula

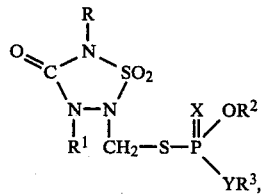

where R, $R^1$, $R^2$, $R^3$, X and Y have the meanings given in the disclosure. The compounds are suitable for combating pests from the class of insects, Acarina and nematodes.

5 Claims, No Drawings

1,2,3,5-THIATRIAZOLIDIN-4(2H)-ONE-1,1-DIOXIDE PHOSPHORIC ACID DERIVATIVES AND THEIR USE FOR COMBATING PESTS

The present invention relates to heretocyclic phosphoric acid derivatives, pesticides containing these compounds as active ingredients, and a process for combating pests with these compounds.

The compounds according to the invention are of the formula

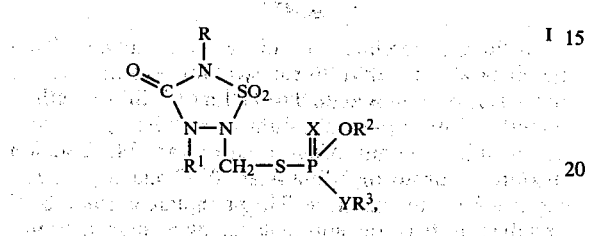

where R denotes unsubstituted or methoxy- or halogen-substituted alkyl of up to 10 carbon atoms or cycloalkyl of from 4 to 8 carbon atoms, $R^1$ denotes alkyl of up to 6 carbon atoms or cycloalkyl of from 4 to 8 carbon atoms, $R^2$ denotes alkyl of up to 5 carbon atoms, $R^3$ denotes alkyl of up to 5 carbon atoms, X denotes oxygen or sulfur, and Y denotes oxygen, sulfur or the bivalent radical —$NR^4$—, $R^4$ denoting hydrogen or alkyl of up to 5 carbon atoms.

The compounds are suitable for combating pests, especially insects Acarina and nematodes. Their action is superior to that of prior art active ingredients from the class of phosphoric acid esters, such as O,O-diethyl-S-(2-chloro-1-phthalimidoethyl)-phosphorodithioate (U.S. Pat. No. 2,984,669) and O,O-dimethyl-S-(N-methylcarbamoylmethyl)-phosphorodithioate (German Pat. No. 819,998). The compounds according to the invention may be used as pesticides in crop protection and in the hygiene, stores protection and veterinary sectors.

In formula I, R denotes linear or branched alkyl of up to 10 carbon atoms, preferably of up to 4 carbon atoms, which is unsubstituted or substituted by methoxy or halogen, such as chlorine, or denotes cycloalkyl of from 4 to 8 carbon atoms. Examples of such radicals are methyl, ethyl, isopropyl, 2-chloroethyl, n-butyl, sec-butyl, isobutyl, cyclobutyl, cyclopentyl, cyclohexyl, cycloheptyl and cyclooctyl.

$R^1$ in formula I is linear or branched alkyl of up to 4 carbon atoms, such as methyl, ethyl, n-propyl, isopropyl, sec-butyl and isobutyl, or is cycloalkyl of from 4 to 8 carbon atoms, such as cyclobutyl, cyclohexyl and cyclooctyl. $R^3$ is linear or branched alkyl of up to 5 carbon atoms, such as methyl, ethyl, n-propyl, isopropyl, n-butyl, n-pentyl and isopentyl. Preferably, $R^2$ is ethyl and $R^3$ butyl.

The heterocyclic phosphoric acid derivatives of the formula I may be obtained by reaction of 1,2,3,5-thiatriazolidin-4(2H)-one-1,1-dioxide derivatives of the formula

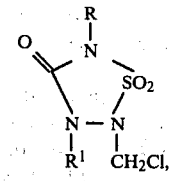

where R and $R^1$ have the above meanings, with a phosphoric acid ester salt of the formula

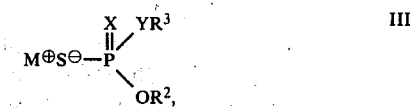

where $R^2$, $R^3$, X and Y have the above meanings and $M^\oplus$ denotes an unsubstituted or substituted ammonium ion an alkali metal ion or one equivalent of an alkaline earth metal ion, in the presence of an inert organic solvent.

Generally, the reaction is carried out at from 10° to 100° C., preferably from 40° to 60° C., depending on the boiling point of the solvent, at atmospheric or superatmospheric pressure and continuously or batchwise.

Examples of suitable solvents are aliphatic and aromatic hydrocarbons, chlorohydrocarbons and nitrohydrocarbons, such as benzene, toluene, xylene, chlorobenzene, chloroform, methylene chloride and carbon tetrachloride; cyclic and acylic ethers, such as diethyl ether and tetrahydrofuran; ketones, such as acetone and cyclohexanone; and nitriles, such as acetonitrile. Mixtures of these solvents may also be used.

Advantageously, equimolar amounts of the starting materials of the formulae II and III are used. In some instances, an excess of the one or the other reaction component may be of advantage.

The 1,2,3,5-thiatriazolidin-4(2H)-one-1,1-dioxide derivatives of the formula II used as starting materials may be obtained by reaction of sulfamyl chlorides of the formula

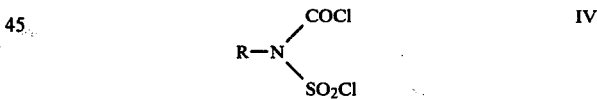

with hydrazines of the formula

to give 1,2,3,5-thiatriazolidin-4(2H)-one-1,1-dioxides of the formula

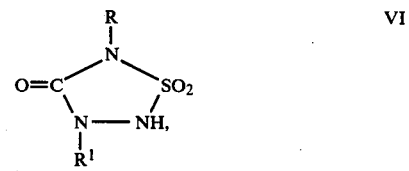

which may be converted into the corresponding chloromethyl-substituted compounds by reaction with formaldehyde and thionyl chloride. In the foregoing formulae, R and $R^1$ have the above meanings (J. Chem. Research, 1977, pp. 2813–2825).

The phosphoric acid ester salts of the formula III are known (Houben-Weyl, Methoden der organ. Chemie, 12/2, 690 et seq., Georg Thieme-Verlag, Stuttgart, 1964).

Suitable cations of these salts are, in addition to the ammonium ion, substituted ammonium ions, e.g., the dimethylammonium and diethylammonium ions, alkali metal ions, e.g., the sodium and potassium ions, and alkaline earth metal ions, eg., the calcium ion.

The preparation of the compounds according to the invention is illustrated by the following examples.

EXAMPLE 1

22 g of formaldehyde (as a 40% formalin solution) is added to 38.6 g of 3-methyl-5-isopropyl-1,2,3,5-thiatriazolidin-4(2H)-one-1,1-dioxide. The reaction mixture is refluxed for a day, and the solid substance which then separates out is triturated with petroleum ether, filtered and dried. 38.1 g of 2-hydroxymethyl-3-methyl-5-isopropyl-1,2,3,5-thiatriazolidine-4(2H)-one-1,1-dioxide is obtained.

NMR data: doublet at 1.5 ppm (6 protons), singlet at 3.25 ppm (3 protons), quartet at 4.25 ppm (1 proton), singlet at 4.85 ppm (2 protons), OH group at 6–6.2 ppm.

29.8 g of thionyl chloride is dripped into 37.5 g of 2-hydroxymethyl-3-methyl-5-isopropyl-1,2,3,5-thiatriazolidin-4(2H)-one-1,1-dioxide in 120 ml of chloroform. The reaction mixture is then refluxed for 5 hours and left to stand overnight. Filtration gives 36 g of 2-chloromethyl-3-methyl-5-isopropyl-thiatriazolidin-4(2H)-one-1,1-dioxide of melting point 58°–64° C.

At room temperature, a solution of 13.6 g of the dimethylammonium salt of O-ethyl-S-sec-butyl-dithiophosphoric acid in 60 ml of acetonitrile is added to 12.1 g of 2-chloromethyl-3-methyl-5-isopropyl-thiatriazolidin-4(2H)-one-1,1-dioxide in 120 ml of acetonitrile. The temperature rises by about 2° C. The mixture is stirred for 4 hours at 40° C., and then overnight at room temperature. The mixture is concentrated and the residue is taken up in either and extracted 3 times with 100 to 150 ml of water. The ether phase is dried, filtered and concentrated. There is obtained 14.2 g of the compound of the formula

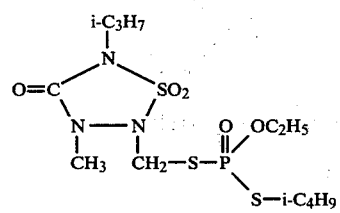

The product is purified by chromatography in a silica gel column (developer: n-hexane, with acetone content increasing up to 8%); $n_D^{25}$:1.5072.

|  | C | H | N | S | P |
|---|---|---|---|---|---|
| calc.: | 34.4 | 6.3 | 10.0 | 22.9 | 7.4 |
| found: | 34.8 | 6.3 | 10.3 | 23.1 | 7.2 |

NMR data: doublet at 4.95 ppm (16 Hz) (2 protons), multiplet at 4.2 ppm (2+1 protons), singlet at 3.25 ppm (3 protons).

EXAMPLE 2

At 30° C., a solution of 15.5 g of the dimethylammonium salt of O-ethyl-S-isobutyldithiophosphoric acid in tetrahydrofuran is added to 12.1 g of 2-chloromethyl-3-methyl-5-isopropyl-1,2,3,5-thiatriazolidin-4(2H)-one-1,1-dioxide in 100 ml of tetrahydrofuran. The reaction mixture is stirred for 3 hours at 50° C. and kept overnight at room temperature. The precipitate is filtered off and the filtrate is concentrated and taken up in dichloromethane. After extraction with water, the dichloromethane phase is dried and concentrated. There is obtained 15.8 g of the compound of the formula

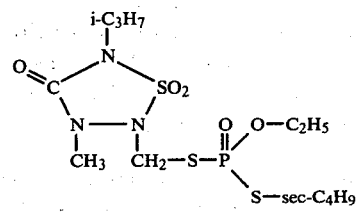

The product is purified in a silica gel column (developer: n-hexane/acetone 8/1); $n_D^{25}$: 1.5121.

|  | C | H | N | S | P |
|---|---|---|---|---|---|
| calc.: | 34.3 | 6.25 | 10 | 22.9 | 7.4 |
| found: | 34.1 | 6.1 | 11.1 | 23.8 | 6.4 |

The following compounds of the formula I, for instance, may be prepared analogously:

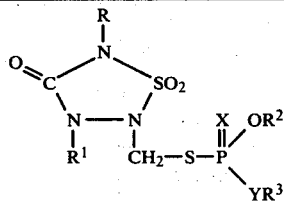

| No. | R | R¹ | R² | R³ | X | Y | $n_D^{25}$ |
|---|---|---|---|---|---|---|---|
| 3 | i-C₃H₇ | CH₃ | n-C₄H₉ | C₂H₅ | O | S | 1.5138 |
| 4 | i-C₃H₇ | CH₃ | i-C₃H₇ | C₂H₅ | O | S | 1.5159 |
| 5 | i-C₃H₇ | CH₃ | n-C₃H₇ | C₂H₅ | O | S | 1.5141 |
| 6 | i-C₃H₇ | CH₃ | C₂H₅ | C₂H₅ | O | O | 1.5151 |

-continued $$\begin{array}{c} R \\ | \\ O=C-N \\ \phantom{O=C-}\diagdown SO_2 \\ N-N \\ | \phantom{N-}| \\ R^1 \phantom{N}CH_2-S-P(=X)(OR^2)(YR^3) \end{array}$$

| No. | R | $R^1$ | $R^2$ | $R^3$ | X | Y | $n_D^{25}$ |
|---|---|---|---|---|---|---|---|
| 7 | i-$C_3H_7$ | $CH_3$ | $C_2H_5$ | $CH_3$ | O | —NH— | |
| 8 | i-$C_3H_7$ | $CH_3$ | $C_2H_5$ | i-$C_3H_7$ | O | —NH— | 1.4950 |
| 9 | i-$C_3H_7$ | $CH_3$ | $C_2H_5$ | $CH_3$ | O | —N($CH_3$)— | 1.4960 |
| 10 | $C_2H_5$ | $CH_3$ | $C_2H_5$ | n-$C_4H_9$ | O | S | 1.5145 |
| 11 | $C_2H_5$ | $CH_3$ | $C_2H_5$ | i-$C_3H_7$ | O | S | 1.5160 |
| 12 | $C_2H_5$ | $CH_3$ | $C_2H_5$ | $C_2H_5$ | S | O | 1.5170 |
| 13 | $C_2H_5$ | $CH_3$ | $C_2H_5$ | n-$C_3H_7$ | O | S | 1.5150 |
| 14 | $C_2H_5$ | $CH_3$ | $C_2H_5$ | sec-$C_4H_9$ | O | S | 1.5140 |
| 15 | $C_2H_5$ | $CH_3$ | $C_2H_5$ | i-$C_4H_9$ | O | S | 1.5140 |
| 16 | $C_2H_5$ | $CH_3$ | $C_2H_5$ | i-$C_3H_7$ | O | —NH— | 1.4981 |
| 17 | $C_2H_5$ | $CH_3$ | $C_2H_5$ | $CH_3$ | O | —N($CH_3$)— | 1.4980 |
| 18 | $CH_3$ | $CH_3$ | $C_2H_5$ | n-$C_4H_9$ | O | S | 1.5202 |
| 19 | $CH_3$ | $CH_3$ | $C_2H_5$ | sec-$C_4H_9$ | O | S | 1.5195 |
| 20 | $CH_3$ | $CH_3$ | $C_2H_5$ | i-$C_4H_9$ | O | S | 1.5200 |
| 21 | $CH_3$ | $CH_3$ | $C_2H_5$ | i-$C_3H_7$ | O | S | 1.5218 |
| 22 | $CH_3$ | $CH_3$ | $C_2H_5$ | $CH_3$ | O | —N($CH_3$)— | 1.5020 |
| 23 | $CH_3$ | $CH_3$ | $C_2H_5$ | i-$C_3H_7$ | O | —NH— | 1.5019 |
| 24 | $CH_3$ | $CH_3$ | $CH_3$ | i-$C_4H_7$ | O | S | 1.5250 |
| 25 | $CH_3$ | $CH_3$ | $CH_3$ | i-$C_4H_9$ | O | S | |
| 26 | i-$C_3H_7$ | i-$C_3H_7$ | $C_2H_5$ | sec-$C_4H_9$ | O | S | 1.5051 |
| 27 | i-$C_3H_7$ | i-$C_3H_7$ | $C_2H_5$ | i-$C_4H_9$ | O | S | 1.5080 |
| 28 | i-$C_3H_7$ | i-$C_3H_7$ | $C_2H_5$ | i-$C_3H_7$ | O | S | |
| 29 | i-$C_3H_7$ | i-$C_3H_7$ | $CH_3$ | | O | S | |
| 30 | $CH_3$ | i-$C_3H_7$ | $C_2H_5$ | sec-$C_4H_9$ | O | S | 1.5155 |
| 31 | $CH_3$ | i-$C_3H_7$ | $C_2H_5$ | i-$C_4H_9$ | O | S | 1.5130 |
| 32 | $CH_3$ | i-$C_3H_7$ | $C_2H_5$ | n-$C_3H_7$ | O | S | m.p. 54–55° C. |
| 33 | $CH_3$ | i-$C_3H_7$ | $C_2H_5$ | i-$C_3H_7$ | O | —NH— | 1.4990 |
| 34 | $CH_3$ | i-$C_3H_7$ | $CH_3$ | i-$C_4H_9$ | O | S | |
| 35 | $CH_3$ | i-$C_3H_7$ | $C_2H_5$ | $C_2H_5$ | S | O | 1.5170 |
| 36 | $C_6H_{11}$ | $CH_3$ | $C_2H_5$ | i-$C_4H_9$ | O | S | |
| 37 | $C_6H_{11}$ | i-$C_3H_7$ | $C_2H_5$ | i-$C_4H_9$ | O | S | |
| 38 | $C_6H_{11}$ | $C_6H_{11}$ | $C_2H_5$ | i-$C_4H_9$ | O | S | |
| 39 | i-$C_3H_7$ | $C_6H_{11}$ | $C_2H_5$ | i-$C_4H_9$ | O | S | |
| 40 | i-$C_3H_7$ | $C_6H_{11}$ | $C_2H_5$ | n-$C_3H_7$ | O | S | |
| 41 | i-$C_3H_7$ | $CH_3$ | $CH_3$ | i-$C_4H_9$ | O | S | |
| 42 | i-$C_3H_7$ | $CH_3$ | $CH_3$ | n-$C_3H_7$ | O | S | 1.5161 |
| 43 | Cl—$CH_2CH_2$— | $CH_3$ | $C_2H_5$ | i-$C_4H_9$ | O | S | |
| 44 | Cl$CH_2CH_2$— | $CH_3$ | $C_2H_5$ | i-$C_3H_7$ | O | S | |

The heterocyclic phosphoric acid derivatives of the formula I according to the invention are suitable for effectively combating pests from the class of insects, Acarina and nematodes.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresis funebrana, Ostrinia nubilalis, Loxostege sticticalis, Ephestia keehniella, Chilo suppressalis, Galleria Mellonella, Malacosoma neustria, Dendrolimus pini, Thaumatopoea pityocampa, Phalera bucephala, Chemimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, lema melanopus, Leptinotarsa decemlineata, Phaedon cochleariae, Phyllotreta nemorum, Chaetocnema tibialis, Phylloides, chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia con icularis, Muscina stabulans, Glossina morsitans, Oes-*

*trus ocis, Chrysomya macellaria, Chrysomya hominivorax, Lucilia cuprina, Lucilia sericata,* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius Dreyfusia nordmannianae, Dreyfusia piceae, Adelges laricis,* and *viteus vitifolii;* examples from the Isoptera order are *Reticulitermes lucifugus, Calotermes flavicollis, Leucotermes flavipes* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Paratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethyl sulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

Examples of formulations are given below:

I. 3 parts by weight of active ingredient no. 1 is intimately mixed with 97 parts by weight of particulate kaolin. A dust is obtained containing 3% by weight of the active ingredient.

II. 30 parts by weight of active ingredient no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of active ingredient no. 4 is dissolved in a mixture consisting of 80 parts by weight of xylene, 10 parts by weight of the adduct of 8 to 10 moles of ethylene oxide with 1 mole of oleic acid-N-monoethanolamine, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of active ingredient no. 5 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

The active ingredients may also be successfully used in the ultra-low volume method, where it is possible to apply formulations containing more than 95 wt% of active ingredient, or even the 100% active ingredient.

There may be added to the individual active ingredients or mixtures thereof (if desired, immediately before use (tankmix)) oils of various types, herbicides, fungicides, insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropane+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thioxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropyl-phosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenylacetonitrile, O,O-diethyl-S-(2-chloro-1-phthalimidoethyl9-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethylO-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4--pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl($\pm$)-cis,trans-2,2-dimethyl-3-(2,2-dichlorovinyl)-cyclopropanecarboxylate, α-cyano-3-phenoxybenzyl($\pm$)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furyl-methyl-chrysanthemate, and α-cyano-3-phen-oxy-benzyl-α-isopropyl-4-chlorophenylacetate.

The following examples illustrate the biological action of the new compounds. The prior art active ingredients O,O-diethyl-S-(2-chloro-1-phthalimido-ethyl)-phosphordithioate (A; U.S. 2,984,669) and O,O-dimethyl-S-(N-methylcarbamoylmethyl)-phosphorodithioate (B; German 819,998) are used for comparison purposes.

EXAMPLE A

Contact action on mosquito larvae (*Aedes aegypti*)

Aqueous emulsions of the active ingredients are added to 200 ml of tapwater and 30 to 40 mosquito larvae in the 4th larval stage are introduced. The temperature is kept at 20° C. The action is assessed after 24 hours.

In this test, compounds nos. 1, 2, 3, 5, 14 and 30 according to the invention have a better action than comparative agent B.

EXAMPLE B

Contact action on cotton stainers (*Dysdercus intermedius*)

Petri dishes 10 cm in diameter are lined with 1 ml of acetonic solutions of the active ingredients.

After the solvent was evaporated, 20 larvae in the penultimate stage are placed in each dish and the action is registered after 24 hours. Compounds nos. 2, 5, 8, 12, 13, 14, 16, 30, 31 and 33 according to the invention have an action superior to that of comparative agent A.

EXAMPLE C

Contact action and effect of ingested food on caterpillars of the diamondback moth (*Plutella maculipennis*)

Leaves of yong cabbage plants are dipped for 3 seconds in aqueous emulsions of the active ingredients, and placed, after excess liquid has been briefly allowed to drip off, on a moist filter paper in a Petri dish. 10 caterpillars in the 4th stage are then placed on each leaf.

The action is assessed after 48 hours; compounds nos. 1, 2, 3, 5, 6, 10, 11, 13, 14, 15, 18, 20, 21, 24, 30, 31 and 42 prove to have a very good action.

EXAMPLE D

Contact action on oriental cockroaches (*Blatta orientalis*)

The bottoms of 1 liter preserving jars are treated with acetonic solutions of the active ingredients. After the solvent has evaporated, 5 adult cockroaches are placed in each jar. The kill rate is determined after 48 hours; it is higher in the case of compounds nos. 1, 5, 13, 14, 30 and 42 according to the invention than in the case of comparative agent A.

EXAMPLE E

Action on spider mites (*Tetranychus telarius*)

Potted bushbeans which have developed the first pair of true leaves and are under heavy attack from spider mites (*Tetranychus telarius*) are sprayed to runoff from all sides in a spray cabinet with 50 ml of aqueous formulations of the active ingredients. Spraying lasts for about 22 seconds.

When the plants are investigated after 8 days for signs of living mites, it is found that a much lower amount of active ingredients nos. 1, 2, 3, 5, 10, 13, 14, 15, 18, 20, 23, 24, 30, 31, 33 and 42 according to the invention is needed to kill the mites than of comparative agent B.

EXAMPLE F

Contact action on ticks (*Ornithodorus moubata*)

Ticks in the 3rd larval stage are placed in paper bags and dipped for 3 seconds in the aqueous emulsion under investigation. The bags are then suspended. The action on the ticks is assessed after 48 hours. A high percentage of the ticks is killed when the emulsion contains 0.005 or 0.01 wt% of active ingredients nos. 1, 2, 3, 8, 13, 15, 16, 18, 20, 23, 30, 31 and 33 according to the invention.

EXAMPLE G

Action on root-knot nematodes (*Meloidogyne incognita*)

Garden soil heavily infested with Meloidogyne incognita is split into 200 g portions which are intimately mixed with 30 ml of aqueous active ingredient formulations and filled into plastic pots. Tomato plants are then placed in the soil prepared in this manner.

After 6 to 8 weeks root attack is assessed. Root-knot formation is prevented by active ingredients nos. 30, 31, 32 and 33, whereas the roots of the control plants are already heavily infested.

We claim:

1. A heterocyclic phosphoric acid derivative of the formula $$\begin{array}{c} R \\ | \\ O=C-N \\ \phantom{O=C-}\diagdown SO_2 \\ \phantom{O=C-}\diagup \\ N-N \phantom{xxx} X \phantom{x} OR^2 \\ | \phantom{xx} | \phantom{xxxxx} \| \diagup \\ R^1 \phantom{x} CH_2-S-P \\ \phantom{R^1 CH_2-S-P}\diagdown YR^3, \end{array} \quad I$$

where R denotes unsubstituted or methoxy- or halogen-substituted alkyl of up to 10 carbon atoms or cycloalkyl of from 4 to 8 carbon atoms, $R^1$ denotes alkyl of up to 6 carbon atoms or cycloalkyl of from 4 to 8 carbon atoms, $R^2$ denotes alkyl of up to 5 carbon atoms, $R^3$ denotes alkyl of up to 5 carbon atoms, X denotes oxygen or sulfur, and Y denotes oxygen, sulfur or the bivalent radical —$NR^4$—, $R^4$ denoting hydrogen or alkyl of up to 5 carbon atoms.

2. 2-(O-Ethyl-S-isobutyl-phosphorylmercaptomethyl)-3-methyl-5-isopropyl-1,2,3,5-thiatriazolidin-4(2H)-one-1,1-dioxide.

3. 2-(O-Ethyl-S-sec-butyl-phosphorylmercaptomethyl)-3-methyl-5-isopropyl-1,2,3,5-thiatriazolidin-4(2H)-one-1,1-dioxide.

4. A composition for combating insects, Acarina and Nematodes which comprises inert additives and a pesticidally effective amount of a heterocyclic phosphoric acid derivative of the formula I as set forth in claim 1.

5. A process for combating insects, Acarina and Nematodes which comprises applying to the pests or their habitat a pesticidally effective amount of a heterocyclic phosphoric acid derivative of the formula I as set forth in claim 1.

* * * * *